United States Patent [19]

Baidwan et al.

[11] Patent Number: 4,466,446
[45] Date of Patent: * Aug. 21, 1984

[54] PLUNGER SUBASSEMBLY FOR BLOOD GAS SYRINGES

[75] Inventors: Balinderjeet S. Baidwan; Dean H. Iwasaki, both of Denver, Colo.

[73] Assignee: Marquest Medical Products, Inc., Englewood, Colo.

[ * ] Notice: The portion of the term of this patent subsequent to Nov. 10, 1998 has been disclaimed.

[21] Appl. No.: 505,707

[22] Filed: Jun. 20, 1983

Related U.S. Application Data

[63] Continuation of Ser. No. 253,402, Apr. 13, 1981, abandoned, which is a continuation-in-part of Ser. No. 162,329, Jun. 24, 1980, Pat. No. 4,299,238.

[51] Int. Cl.³ ............................................. A61B 5/14
[52] U.S. Cl. ................................. 128/765; 604/125; 604/190; 604/236
[58] Field of Search ............... 128/762, 763, 765, 766; 604/122, 124, 125, 126, 190, 228, 231, 236, 406

[56] References Cited

U.S. PATENT DOCUMENTS

| | | | |
|---|---|---|---|
| 1,924,916 | 8/1933 | Drake | 604/228 |
| 3,943,917 | 3/1976 | Johansen | 128/763 |
| 4,326,540 | 4/1982 | Bailey et al. | 128/763 |
| 4,327,745 | 5/1982 | Ford | 128/765 |
| 4,340,067 | 7/1982 | Rattenborg | 128/763 |

*Primary Examiner*—Kyle L. Howell
*Assistant Examiner*—Max F. Hindenberg

[57] ABSTRACT

This invention relates to an improved plunger subassembly for use in a blood gas syringe barrel characterized by a pushrod having a piston on its front end with a hollow interior defining a fluid collection chamber communicating with both the front and rear ends thereof by passageways blocked by a filter that will pass gases but is impervious to fluids. With the plunger subassembly in its passive state, blood and gas entering the syringe barrel from the front is free to enter the collection chamber by means of slits on the periphery of the piston at its front end. The contaminated blood that has been in contact with the air originally in the syringe barrel is trapped in the fluid collection chamber inside the piston while the gases pass on through the filter and are vented to the atmosphere. Opposed surfaces on the pushrod and piston cooperate to define an air-tight seal effective to prevent the flow of air past the piston when the plunger subassembly is actuated to retract same.

13 Claims, 6 Drawing Figures

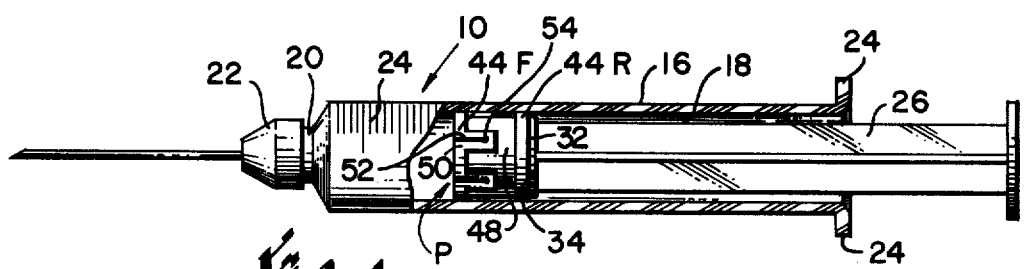
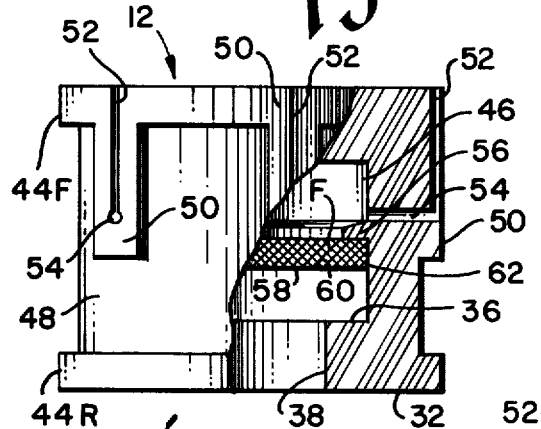
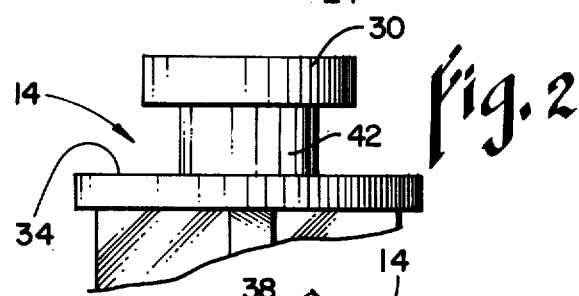
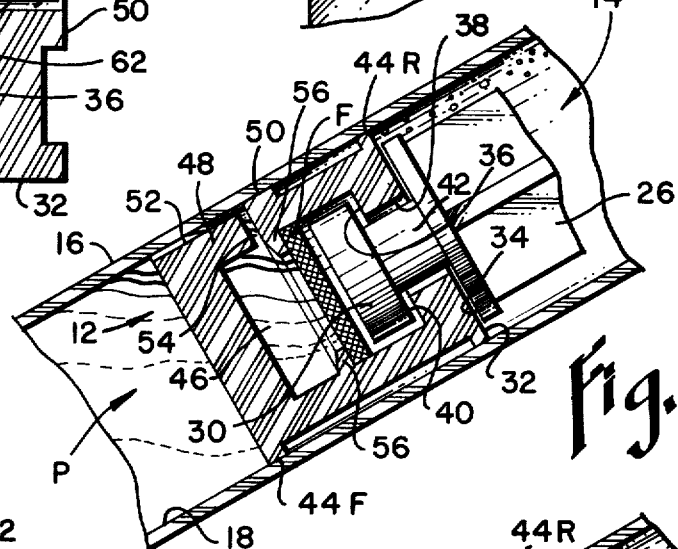
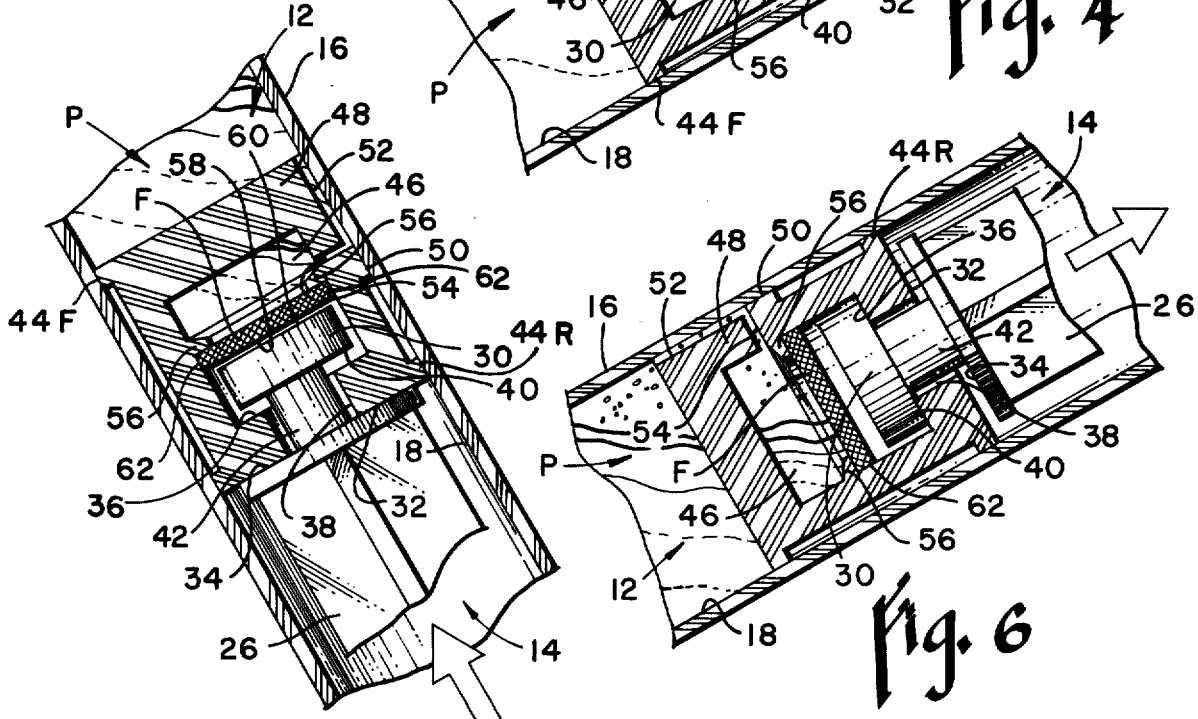

PLUNGER SUBASSEMBLY FOR BLOOD GAS SYRINGES

This is a continuation of application Ser. No. 253,402, filed Apr. 13, 1981, which is a continuation-in-part of Ser. No. 162,329, filed June 24, 1980, now U.S. Pat. No. 4,299,238. Continuation-in-part application Ser. No. 253,402, is now abandoned.

In our copending U.S. patent application Ser. No. 162,329 filed June 24, 1980 now U.S. Pat. No. 4,299,238, we disclosed a vented piston and pushrod subassembly for use in a conventional syringe barrel which cooperated with one another in their so-called passive condition to vent air being pushed ahead of the incoming blood sample while, at the same time, preventing the blood from exiting the syringe by the same route. The contaminated portion of the sample taken due to its contact with the air in the barrel ended up trapped inside the piston where it had no effect upon the rest of the sample used for analysis. The resulting syringe was thought to be ideally suited for blood gas analysis and, as a matter of fact, it still is, provided certain conditions are met in its manufacture.

From a commercial standpoint, one of the interesting features of our earlier design was the fact that it made use of a commercially available syringe, the pushrod and particularly the piston of which were redesigned so as to cooperate with one another in a novel and unexpected fashion to realize objectives heretofore unattainable by the prior art blood gas syringes. In order to accomplish these ends; however, it was necessary that certain critical dimensional relationships exist between the pushrod tip and piston carried thereby effective to vent air while, at the same time, blocking the movement of the blood sample. More specifically, a continuous annular fluid-tight seal effective to block the flow of blood while passing air had to be established between opposed mating surfaces of the piston and pushrod head while these elements were in the passive state and the patient's arterial pressure alone was moving the blood sample into the syringe and sweeping the air out. Unexpectedly, it has recently been discovered that due to tolerance variations in these manufactured parts, a significant number of piston and pushrod subassemblies failed to fit tightly enough to establish the annular fluid seal or, alternatively, fit so tightly that no air could escape. While these problems are rather easily solved by merely holding tighter tolerances during manufacture, we have unexpectedly come up with a different solution to the problem which is not dependent upon the formation of the continuous annular liquid seal of our earlier blood gas syringe. Instead, a still further modified piston contains a filter in the hollow interior thereof that has flow passages therethrough so small that it will not pass the blood yet large enough to pass air. This filter is spaced in front of the flattened head on the tip of the pushrod where it is retained by a suitable stop-forming retainer so as to not block the outlets of the passages bringing air and blood into the hollow interior of the piston. The piston is loosely retained on the reshaped head of the pushrod so as to leave abundant space for the escape of air therebetween and back along the stem to the atmosphere. It will become apparent that because the piston is modified to include the filter disc, the dimensional problems of the type previously encountered become insignificant. While an extra part, namely, the filter, is required in the assembly, it can be inserted into the hollow interior of the piston in a matter of seconds just before the latter is attached to the pushrod so that the overall increase in material and labor cost is minimal. In fact, the necessary tightening of manufacturing tolerances and the resultant inspection to assure they have been met would, in all probability make our earlier syringe the more expensive of the two.

Now, applicants are aware of the fact that certain syringes exist which incorporate filters capable of passing the air trapped between the incoming blood sample and the piston out through the rear end. The two prior blood sample collection units known to applicants that incorporate such a feature are the "Deseret" and the "Pharmaseal" ones.

The Deseret unit is true syringe and is made in Utah by the Deseret Company. It incorporates a filter in the front end of the plunger exposed on one side to the incoming blood sample and on the other to the atmosphere. The filter, of course, blocks the flow of blood but, being pervious to gases, it allows them to flow both ways. The problem, therefore, starts when the blood enters the syringe barrel where it immediately comes into contact with the air already there and becomes contaminated. This would not be too serious if it were possible to separate the blood thus contaminated from that which will be used in the blood gas analysis. Unfortunately, the Deseret Syringe makes no provision for this eventuality and, instead, the contaminated blood remains at all times mixed with the blood that will be analyzed for the simple reason that it cannot get past the filter.

The other problem with the Deseret syringe is the fact that even with no air bubble left in the barrel, only blood, a situation exists where there is blood on one side of the filter and room air on the other. Since the filter is ineffective to prevent air from moving through it, air does, in fact, go from the atmosphere side of the filter forwardly through into the barrel where it comes into contact with and contaminates the sample. Tests run by applicants have shown that the longer a sample is left in the Deseret syringe, the more inaccurate the analysis becomes. More specifically, the sample demonstrates an increasing oxygen content as the room air continues to enter same through the filter as above noted. On the other hand, the carbon dioxide concentration gets smaller as time goes on since it comes out of solution and escapes past the filter to the atmosphere.

The Pharmaseal blood sample collector made in California by the Pharmaseal Laboratories is not a syringe in the popular sense in which this term is used because it has no plunger. Like the Deseret syringe, it has some deficiencies also; however, for the most part they are of a mechanical nature since the unit is, under the proper circumstances, fully capable of taking and preserving a good blood sample for blood gas analysis purposes. Its filter is located at the extreme rear end of a flexible tube which forms the barrel. In theory at least, arterial pressure is depended upon to fill the tube to a point well beyond where the tube is clamped off to separate the contaminated blood behind the clamp from that which will be analyzed ahead thereof. No provision is made for sucking the sample into the barrel as it contains no plunger subassembly whatsoever.

The first problem arises in connection with the size of the sample that must be taken. While a very small uncontaminated sample is adequate for purposes of a blood gas analysis, the Pharmaseal syringe demands that one much larger than necessary be taken, first to fill the rigid neck of the tip to which the needle is attached and, secondly, so that the clamp can be used to separate the contaminated portion of the sample from the uncontaminated one.

Also, as a practical matter, the technician must decide in advance just what size sample is going to be taken and set the clamp along the barrel accordingly. If, as occasionally occurs, the patient's arterial pressure is inadequate to fill the barrel beyond the preselected clamping point, the whole procedure must be repeated since the contaminated portion of the sample cannot be separated from the uncontaminated one.

The next problem arises when the needle is removed because the technician must use one hand to immediately stem the flow of blood from the patient's artery by applying pressure at the site. This leaves one hand to actuate the clamp and isolate the uncontaminated portion of the sample which is not all that easy to do.

Finally, when clamping off the barrel, experience has shown that this operation causes blood to squirt from the needle which is not only messy but, in addition, a possible way of spreading infection, particularly hepatitis. Furthermore, unless the sample taken extends back into the barrel well beyond the clamp, it is sometimes difficult to tell whether or not an air bubble might have been left ahead thereof since the actual clamped area is not only obscured by the clamp but by the sample as well. Other problems associated with the plungerless Pharmaseal syringe are detailed in our earlier application.

Applicants have now discovered that by combining the features of their previous syringe, by means of which the contaminated blood is trapped inside the hollow piston, with the filter that will pass the gaseous components while blocking the blood, a significantly improved syringe results that has none of the tolerance problems associated with their earlier one, yet, which produces a blood gas sample every bit as contamination-free as before. Moreover, the technique of using the syringe remains unchanged and is far simpler than that of the Pharmaseal syringe previously mentioned.

It is, therefore, the principal object of the present invention to provide a novel and improved syringe.

A second objective is to provide a syringe that is ideally suited for use in taking blood samples for blood gas analysis.

Another objective of the within disclosed invention is to provide a syringe wherein the portion of the incoming blood that becomes contaminated with the air already in the barrel is isolated and kept separate from that which is analyzed.

Still another object is to provide a blood gas syringe wherein any air re-entering the syringe and coming into contact with the blood sample can only contact that portion of the sample that has already been contaminated and, for this reason, will not be used in the analysis.

An additional objective is that of providing a syringe of the class described which keeps the sample out of contact with the technician so as to remove the opportunity for infection from this source when properly handled.

Further objects are to provide a blood gas syringe, and more specifically an improved piston and pushrod subassembly for use with a conventional syringe barrel that is compact, safe and easy to use, simple, lightweight, versatile and even somewhat decorative.

Other objects will be in part apparent and in part pointed out specifically hereinafter in connection with the description of the drawings that follows, and in which:

FIG. 1 is an elevation of the improved syringe, portions of the barrel having been broken away to reveal the piston and pushrod subassembly;

FIG. 2 is an enlarged fragmentary view showing the head of the pushrod in elevation;

FIG. 3 is an elevational view to the same scale as FIG. 2 showing the piston, portions thereof having been broken away and shown in section;

FIG. 4 is a fragmentary diametrical section to a scale smaller than that of FIGS. 2 and 3 but larger than FIG. 1 showing the passive condition of the syringe which it occupies when arterial pressure is being used to fill the barrel and hollow piston with blood;

FIG. 5 is a fragmentary diametrical section to the same scale as FIG. 4 showing the pushrod being actuated forwardly to extend the piston and expel the uncontaminated portion of the blood sample; and, FIG. 6 is a fragmentary diametrical section to the same scale as FIGS. 4 and 5 but showing the pushrod being retracted along with the piston mounted thereon so as to establish a continuous annular air-tight seal effective to suck blood from the patient into the barrel when arterial pressure is insufficient to do so.

Referring next to the drawings for a detailed description of the present invention and, initially, to FIGS. 1, 2, and 3 for this purpose, reference numeral 10 has been chosen to broadly designate the blood gas syringe in its entirety while numerals 12 and 14 similarly designate the piston and pushrod thereof, respectively. The barrel 16 is of standard design having a hollow cylindrical bore 18 open at the rear end to receive both the piston 12 and its associated pushrod. The barrel is "necked down" at the front end as shown at 20 in FIG. 1 to detachably receive the needle 22. Suitable volumetric measuring indicia 24 are shown in FIG. 1 inscribed upon the barrel. The rear end of the barrel is shown provided with flanges 24 (FIG. 1 again) that allow the barrel to be grasped and retained between two fingers while the pushrod 14 is actuated to extend same with the thumb of the same hand thereby ejecting the contents through the hollow needle 22 in the well-known manner.

FIGS. 1 and 2 show the pushrod 14 which, in contrast to that of our earlier design, has been reshaped such that certain of its structural features take on new significance as they cooperate in a new way with the redesigned piston 12 to bring about a novel and unexpected result. The piston 12 and pushrod 14 cooperate in assembled relation to produce a plunger subassembly shown in FIGS. 1, 4, 5 and 6 that will be referred to broadly by the letter "P". The pushrod portion of the plunger subassembly P has a handle portion 26 which, in the particular form shown, loosely telescopes into the barrel and cooperates therewith in extended position to maintain the piston 12 in axial alignment therein. The changes in the pushrod are all contained within the head at the front end thereof which has been designated by reference numeral 30. The rear end of handle 26 carries a thumbrest 32 (FIG. 1) for actuating the plunger assembly P into extended position or, alternatively, to retract same while holding the barrel in one hand and pulling the pushrod with the other.

As best seen in FIGS. 4, 5 and 6, piston 12 has a rearwardly-facing annular surface 32 which, when assembled onto the head 30 of the pushrod as shown, opposes a forwardly-facing abutting surface at the front end of the handle 26 and enables plunger subassembly P to be actuated in a manner to extend same as shown in FIG. 5. A continuous annular air-tight seal is formed between annular surface 36 bordering the entryway 38 into the hollow interior of the piston and the forwardly-facing annular surface 50 surrounding the neck 42. This neck projects forwardly from the front end of the handle 26 through the entryway into the hollow interior of the piston where head 30 is housed. The latter seal is formed upon retractable movement of the plunger subassembly P while the annular ribs 44F and 44R encircling opposite ends of the piston lie in annular wiping contact with the cylindrical bore 18 of the barrel as shown in FIG. 6.

In FIG. 2 it can be seen that the head 30 on the tip of the pushrod is considerably larger than the neck 42 that supports same. Neck 42 is sized to be loosely received within the entryway 38 into the hollow interior of the piston as shown in FIGS. 3, 4 and 5. In like manner, while head 30 on the top of the pushrod is considerably larger than entryway 38, it is loosely received within the fluid collection chamber 46 inside the piston because, as will be shown presently, air must be able to escape freely from this pocket around the head, back along neck 42 and out into the rear end of the barrel between opposed surfaces 32 and 34 when the plunger subassembly P is in the relaxed or passive condition of FIG. 4. On the other hand, the enlarged head 30 on the top of the pushrod is sized to engage the forwardly-facing ledge 36 bordering the entryway 38 and opening into chamber 46 because, otherwise, there would be no interengageable surfaces capable of retracting the piston when the pushrod is retracted as shown in FIG. 6.

Looking next at FIG. 3, it will be seen that piston 12 comprises a hollow body 48 bordered at the front by interrupted annular wiping rib 44F and at the rear by continuous annular wiping rib 44R. Ribs 44 are deemed preferable to a continuous cylindrical body all of which is in sliding contact with the barrel bore because the frictional forces in the latter instance become so great that the plunger subassembly becomes difficult to retract and extend. It is for this reason that most areas of the body 48 are recessed beneath ribs 44 so as to remain out of contact with the barrel bore. In the particular form illustrated, longitudinally-extending integral lands 50 extend rearwardly from front rib 44F part way along the body 48 in angularly-spaced relation to one another. These lands also lie in wiping contact with the barrel bore and each contains a forwardly-opening slit 52. At the rear end of each slit is a passage 54 connecting the latter with the fluid collection chamber 46 in the interior of the piston. The net effect of these slit lands 50 and connecting passages 54 is the same as that of the slits 70 in rib 62 along with slit 74 in the body 66 of our earlier unit, namely, that of admitting blood and air into the pocket 46 of the piston under the influence of a positive pressure gradient ahead of the latter.

Piston 12 must be fabricated from rubber or other synthetic elastic material that is impervious to gases, particularly oxygen and carbon dioxide, the precise percentage of which are two of the determinations made in a blood gas analysis. The flexibility is, of course, required, first, so that at least the rear rib 44R remains in fluid and air-tight wiping contact with the barrel bore and, secondly, so that the entryway 38 will stretch to the degree required to accept the enlarged head 30 on the pushrod tip when the plunger subassembly is assembled preparatory to inserting same into the barrel.

In FIGS. 2-6, inclusive, a stop-forming integral abutment is provided inside collection chamber 46 just behind the outlets of passages 54. The sole function of this abutment is to engage the front marginal edge of filter F as shown and prevent the latter from blocking passages 54 where the blood and air enter. It would, of course, be possible to make filter disc F slightly oversize in relation to the diameter of chamber 46 thus relying upon the stretched wall of the piston body to hold the filter in place; however, the abutment is preferred as it provides positive assurance that no blood gets past the filter.

Filter F is not, per se, novel in that it is of the same general type found in the previously described Deseret and Pharmaseal blood collection units, namely, one having the ability to pass gaseous constituents like oxygen and carbon dioxide freely in either direction while, at the same time, blocking the passage of blood.

The thickness of filter F is preferably somewhat less than the axial distance separating the forwardmost extremity of the pushrod from abutment 56. By so doing, when the filter is pushed forwardly up tight against abutment 56, a space will be left between the rear face 58 of the filter and the front face 60 of the pushrod head that will accommodate a small amount of relative axial movement of the pushrod into extended position (FIG. 5) so as to establish the engagement between opposed surfaces 32 and 34 required to move piston 12 into extended position. The gap shown between surfaces 58 and 60 in FIG. 5 is exaggerated for purposes of illustration and, as a practical matter, little if any, gap will exist at this point when the plunger subassembly is being actuated into extended position.

The peripheral edge 62 of the filter should, ideally, lie in continuous annular sealed engagement with the wall of the chamber 56 bordering same so as to insure that no blood can get past the filter if, perchance, it moves out of annular sealed contact with stop-forming abutment 56. This, of course, is easily accomplished by making filter disc F slightly oversize so that it stretches the piston wall slightly.

Now, the most important dimensional relationship of the parts of the plunger subassembly P is that shown in FIG. 4 to which detailed reference will next be made. This is the so-called passive condition of the syringe used to take an arterial blood sample using arterial pressure which gets the blood out of the patient and into the barrel. Note that the slits 52 in the piston are located all the way around the latter as was the case with our earlier unit so that the syringe need not be held in any particular rotational position to insure that no bubble of air is trapped ahead of the piston that cannot escape into the hollow interior thereof through an appropriately located slit. Accordingly, the technician need only set the plunger subassembly to take the size sample he or she wants, place the needle 22 into the patient's artery and let the blood flow into the heparin-coated barrel. As the blood enters the barrel, it, of course, contacts the air present therein and becomes contaminated thereby such that it is unsuitable for use in the blood gas analysis. This contaminated portion of the blood pushes the trapped air ahead thereof and into the uppermost slit 52 where it enters blood collection chamber 46 through the passage 54 connected thereto. Slits 52 and passages 54 are all sized to pass blood as well as air. Once the contaminated blood reaches chamber 46 it is stopped by filter F while the air passes right on through the latter, around head 30 and between opposed surfaces 36 and 40; along neck 42 in the space left between the latter and the wall of the entryway 38, out between opposed surfaces 32 and 34, and back along the handle 26 to the atmosphere. It is important to note that in the relaxed condition of the plunger subassembly shown in FIG. 4, no air-tight seal exists either between opposed surfaces 36 and 40 or between opposed surfaces 32 and 34.

Once chamber 46 contains the contaminated blood as shown in FIG. 5 the plunger subassembly P can be actuated to extend the piston and expel the uncontaminated portion of the sample ahead of piston 12 back out through the needle and into the blood gas analyzer. Note that while air can enter the open rear end of the syringe barrel and work its way all the way forward and through filter F from the back side so as to contact the blood present in chamber 46, this blood is already contaminated and will not be used in the analysis, therefore, any gas passing to and fro through filter F has no effect upon the results.

At this point it is, perhaps, worthy of mention that prior art syringes are known which, undoubtedly, are capable of establishing an air-tight seal between surfaces 36 and 40 upon retraction thereof; however, such a seal is functionally insignificant in that the exterior wiping surfaces of the piston maintain the only seal needed since no passage exists for either the fluids or the air to enter the hollow interior of the piston. Before leaving FIGS. 4 and 5, it is significant that rear rib 44R of the piston lies in continuous annular air and fluid-tight wiping engagement with the barrel bore at all times so nothing can escape past the piston using this route. Also, should the patient's arterial pressure be inadequate to fill the syringe barrel to the preselected level, nothing is lost because the technician need only advance the plunger subassembly manually while holding the needle down and blocking the open end thereof to move the air and contaminated blood into collection chamber 46. This will probably only be necessary if the patient has insufficient arterial pressure to fill the syringe within a reasonable time frame, the better technique being that shown in FIG. 6 of manually retracting the plunger subassembly to aspirate blood into the syringe.

Aspirating blood into the syringe becomes possible due to the air-tight seal established between opposed surfaces 36 and 40 when the pushrod is manually actuated into retracted position. If it were not for such a seal, air could flow past the piston reversing the path it follows in the passive condition described in FIG. 4 so that no vacuum could be established ahead thereof. Once the sample has been aspirated into the syringe as shown in FIG. 6, the plunger subassembly may have to be extended again with the needle held down and closed to get the air out and the contaminated blood into chamber 46 provided the vacuum is insufficient to accomplish the foregoing automatically.

What is claimed is:

1. Apparatus for attachment to a hollow needle and used for obtaining an arterial blood sample when arterial pressure is insufficient to fill a blood-receiving space defined in the apparatus, comprising:
   a syringe barrel having an inner surface and an open rear end and a necked down front end and a longitudinal axis extending from said rear end to said front end;
   plunger means located within said syringe barrel and having a top portion and being movable relative to said syringe barrel, said plunger means being moved to define a blood-receiving space formed between said top portion of said plunger means and said front end of said syringe barrel;
   said plunger means having at least one continuous annular surface in sealing engagement with the inner surface of said syringe barrel at all times during the obtaining of said blood sample; and
   said plunger means including a pushrod and a piston having a hollow interior, said piston being joined to said pushrod with a fluid impervious portion of said pushrod in said hollow interior, said piston and said pushrod cooperating to define a first position in which a passageway between said piston and said pushrod is provided for the movement of gas from the blood-receiving space through at least a portion of said interior of said piston to the ambient environment of the syringe barrel, means permitting limited movement of said pushrod relative to said piston in a direction substantially parallel to said longitudinal axis to define a second position in which said passageway is closed, said passageway being closed for use in aspirating blood into the syringe.

2. Apparatus, as claimed in claim 1, wherein:
   said piston includes a first surface and said pushrod includes a first surface, said piston first surface and said pushrod first surface engaging each other in said second position for use in closing off the blood-receiving space to the ambient environment of the syringe.

3. Apparatus, as claimed in claim 1, further including:
   filter means in said plunger means for preventing the passage of blood therethrough but permitting the passage of air.

4. Apparatus, as claimed in claim 3, wherein:
   said filter means is located within said piston.

5. Apparatus, as claimed in claim 1, wherein:
   said piston has a top portion in which a number of slits are formed for permitting blood and air to flow therepast.

6. Apparatus, as claimed in claim 1, wherein:
   said piston includes an opening formed in a section thereof to provide a path for blood and air into said hollow interior of said piston.

7. Apparatus, as claimed in claim 1, wherein:
   said piston is substantially less in length than said pushrod.

8. A method for obtaining a blood sample from an artery when arterial pressure is insufficient to provide a desired blood sample comprising:
   providing apparatus capable of being attached to a hollow needle, said apparatus including a syringe barrel having an inner surface and having an open rear end and a necked down front end with a longitudinal axis extending therebetween and plunger means movable relative to said syringe barrel said plunger means including only a single pushrod and a single piston joined together;
   providing said plunger means with at least one continuous surface in sealing engagement with the inner surface of said syringe barrel and maintaining said sealing engagement at all times during the obtaining of said blood sample;
   setting said plunger means at a desired position in the syringe barrel to define a blood-receiving space;

providing a passageway through at least a portion of said plunger means to provide a path for gas between the blood-receiving space and the atmosphere;

receiving blood from the artery into the blood-receiving space;

determining whether the arterial pressure is sufficient to obtain the desired sample of blood;

moving at least a portion of said plunger means in a direction substantially parallel to said longitudinal axis to close said passageway so that the blood-receiving space no longer communicates with the atmosphere, when it is determined that arterial pressure is not sufficient to obtain the desired sample; and continuing movement of said plunger means in the same direction creating reduced pressure in the blood-receiving space because of the movement of said plunger means so that blood is aspirated into the blood-receiving space from the artery.

9. A method for obtaining a blood sample from an artery when arterial pressure is insufficient to provide a desired blood sample comprising:

providing apparatus capable of being attached to a hollow needle, said apparatus including a syringe barrel having an inner surface and an open rear end and a necked down front end with a longitudinal axis extending therebetween, and plunger means movable relative to said syringe barrel, said plunger means including a piston having a hollow interior and a pushrod joined to said piston;

providing said piston with at least one continuous surface in sealing engagement with the inner surface of said syringe barrel and maintaining said sealing engagement at all times during the obtaining of said blood sample;

setting said piston at a desired position in the syringe barrel to define a blood-receiving space;

providing a passageway between said piston and said pushrod to provide a path for gas between the blood-receiving space and the atmosphere;

receiving blood from the artery into the blood-receiving space;

determining whether the arterial pressure is sufficient to obtain the desired sample of blood;

grasping and pulling back said pushrod to move said pushrod relative to said piston in a direction substantially parallel to said longitudinal axis to close the gas passageway between said piston and said pushrod, when it is determined that arterial pressure is not sufficient to obtain the desired blood sample; and continue grasping and pulling back of said pushrod in the same direction to move said piston to create a vacuum for aspirating blood into the space in the syringe barrel.

10. A method, as claimed in claim 9, further comprising the steps of:

providing filter means in said plunger means for preventing the passage of blood therethrough but permitting the passage of air.

11. A method, as claimed in claim 9, wherein:

moving said piston in the syringe barrel only by moving said pushrod.

12. A method, as claimed in claim 9, wherein:

making said piston to have a longitudinal extent substantially less than the longitudinal extent of said pushrod.

13. A method for obtaining a blood sample from an artery when arterial pressure is insufficient to provide a desired blood sample comprising:

providing apparatus capable of being attached to a hollow needle, said apparatus including a syringe barrel having an inner surface and an open rear end and a necked down front end with a longitudinal axis extending therebetween and plunger means movable relative to said syringe barrel, said plunger means including only a single pushrod and a single piston joined together;

providing said piston with at least one continuous surface in sealing engagement with the inner surface of said syringe barrel and maintaining said sealing engagement at all times during the obtaining of said blood sample;

providing a passageway between said piston and said pushrod to provide a path for gas between said front end of said syringe barrel and the atmosphere;

receiving blood from the artery into the portion of said syringe barrel between said front end and said piston;

determining whether the arterial pressure is sufficient to obtain the desired sample of blood, said pushrod being maintained in the same position relative to said piston when it is determined that arterial pressure is sufficient to obtain the desired sample;

moving at least a portion of said plunger means in a direction substantially parallel to said longitudinal axis to close said passageway so that any space between said front end of said syringe barrel and said top portion of said piston no longer communicates with the atmosphere, when it is determined that arterial blood pressure is not sufficient to obtain the desired sample; and continuing movement of said plunger means in the same direction creating reduced pressure so that blood is aspirated into said front end of said syringe barrel.

* * * * *